US012221623B2

(12) United States Patent
Gilligan et al.

(10) Patent No.: US 12,221,623 B2
(45) Date of Patent: Feb. 11, 2025

(54) METHODS OF PROCESSING SPERM FOR SEX SORTING (71) Applicant: INGURAN, LLC, Navasota, TX (US)

(72) Inventors: Thomas Boyd Gilligan, College Station, TX (US); Kenneth Michael Evans, College Station, TX (US); Richard Lenz, College Station, TX (US); Clara Gonzalez-Marin, Navasota, TX (US); Ramakrishnan Vishwanath, Hamilton (NZ)

(73) Assignee: INGURAN, LLC, Navasota, TX (US)

( * ) Notice: Subject to any disclaimer, the term of this patent is extended or adjusted under 35 U.S.C. 154(b) by 78 days.

(21) Appl. No.: 13/784,578

(22) Filed: Mar. 4, 2013

(65) Prior Publication Data
US 2014/0099627 A1   Apr. 10, 2014

Related U.S. Application Data (60) Provisional application No. 61/710,343, filed on Oct. 5, 2012.

(51) Int. Cl.
*C12N 5/076* (2010.01)
*C12N 5/071* (2010.01)
*C12Q 1/6806* (2018.01)

(52) U.S. Cl.
CPC .......... *C12N 5/061* (2013.01); *C12N 5/0612* (2013.01); *C12Q 1/6806* (2013.01)

(58) Field of Classification Search
CPC .............................. C12N 5/0612; C12N 5/061
USPC .................................................... 435/2, 40.5
See application file for complete search history.

(56) References Cited

U.S. PATENT DOCUMENTS

| | | | |
|---|---|---|---|
| 4,559,309 | A | 12/1985 | Evenson et al. |
| 6,524,860 | B1 | 2/2003 | Seidel et al. |
| 7,208,265 | B1 | 4/2007 | Schenk |
| 7,582,432 | B2 | 9/2009 | Cook et al. |
| 7,799,569 | B2 | 9/2010 | Durak et al. |
| 7,838,210 | B2 | 11/2010 | Ludwig et al. |
| 7,838,509 | B2 | 11/2010 | Ellington et al. |
| 2005/0003472 | A1 | 1/2005 | Anzar et al. |
| 2005/0244805 | A1 | 11/2005 | Ludwig et al. |
| 2006/0067916 | A1 | 3/2006 | Schenk et al. |
| 2006/0121440 | A1 | 6/2006 | Schenk et al. |
| 2007/0092860 | A1 | 4/2007 | Schenk |
| 2007/0117086 | A1 | 5/2007 | Evans et al. |
| 2009/0053821 | A1* | 2/2009 | Laikhter et al. |
| 2009/0176271 | A1 | 7/2009 | Durack et al. |
| 2011/0236923 | A1 | 9/2011 | Hashemi |
| 2013/0084558 | A1 | 4/2013 | Evans et al. |
| 2014/0099628 | A1 | 4/2014 | Evans et al. |

FOREIGN PATENT DOCUMENTS

| | | | |
|---|---|---|---|
| WO | 9905504 | A2 | 2/1999 |
| WO | 02/41906 | A2 | 5/2002 |
| WO | WO 2004/009237 | * | 1/2004 |
| WO | 2004012837 | A3 | 2/2004 |
| WO | 2009/014456 | A1 | 1/2009 |
| WO | 2009031831 | A2 | 3/2009 |
| WO | 2012014142 | A2 | 3/2009 |
| WO | 2011/053727 | A2 | 5/2011 |
| WO | 2011123166 | A2 | 10/2011 |
| WO | 2010/150013 | A2 | 12/2012 |
| WO | 2013/49631 | | 4/2013 |

OTHER PUBLICATIONS

Lardy et al. (1943). Effect of pH and certain electrolytes on the metabolism of ejactulated spermatozoa. American Journal of Physiology, v135(8), p. 741-746.*
Johnsi et al. (2010). Fluorescence quenching of Tris(2,2'-bipyridine)Ruthenium(II) Dichloride by certain organic dyes. J. Solution Chem, v39, p. 1520-1530.*
Johnson et al. The Beltsville Sperm Sexing Technology: High-Speed Sperm Sorting Gives Improved Sperm Output for In Vitro Fertilization and AI. J. Anim. Sci., v77, p. 213-220.*
Paulenz et al. Comparison of fertility results after vaginal insemination using different thawing procedures and packages for frozen ram semen. Acta Veterinaria Scandinavica 2007, 49:26, 7 pages.*
Gardner et al. Effect on Semen Dilution on Bovine Sperm Viability as Determined by Dual-DNA Staining and Flow Cytometry. Journal of ANdrology, 18(3), 324-331. (Year: 1997).*
Gundogan et al. Influence of sperm concentration on the motility, morphology, membrane and DNA integrity along with oxidative stress parameters of ram sperm during liquid storage. Animal Reproduction Science 122 (2010) 200-207. (Year: 2010).*
Kondracki et al. The Effect of Sperm Concentration in the Ejaculate on Morphological Traits of Bull Spermatozoa. Folia biologica (Kraków), vol. 60 (Jan. 2012), No. 1-2, 85-91 (Year: 2012).*
Stap et al., "Improving the Resolution of Cryopreserved X-and Y-Sperm During DNA Flow Cytometric Analysis with the Addition of Percoll to Quench the Fluorescence of Dead Sperm" J. Anim. Sci., 1998, 76, 1896-1902.
Klinc, "Improved Fertility of Flowcytometrically Sex Selected Bull Spermatozoa" Inaugural-Dissertation, 2005, 1-108.
Rath et al., "Improved quality of sex-sorted sperm: A prerequisite for wider commercial application" Theriogenology, 2009, 71, 22-29.
Klinc et al., "Reduction of Oxidative Stress in Bovine Spermatozoa During Flow Cytometric Sorting" Reprod Dom Anim, 2007, 42, 63-67.

(Continued)

Primary Examiner — Sean C. Barron
(74) Attorney, Agent, or Firm — Ryan Christensen; Hashim Rahman (57) ABSTRACT Methods for processing and sorting sperm are disclosed. Portions of sperm sorting or staining processes may include standardizing sperm samples by adjusting the concentration of the sperm sample to a predetermined concentration and adjusting the pH of the sample to a predetermined value. Sperm may also be stained in a single staining buffer having a DNA selective dye and a quenching dye.

22 Claims, 3 Drawing Sheets (56) References Cited

OTHER PUBLICATIONS

Johnson, Lawrence A., and Welch, Glenn R., "Evaluation of Bisbenzimidazole Analogs For Use in Flow Cytometic DNA Analysis of X-and Y-Bearing Sperm." U.S. Dept. of Agriculture, ARS, Reproduction Lab, Beltsville, MD USA, 1991, p. 86.
McNutt, Tamara L. and Johnson, Lawrence A., "Flow Cytometric Sorting of Sperm: Influence on Fertilization and Embryo/Fetal Development in the Rabbit," Molecular Reproduction and Development, 43, 1996, pp. 261-267.
Montano, G.A., Kraemer, D.C., Robeck, T.R., and O'Brien, J.K., "Evaluation of motility, membrane status and DNA integrity of frozen-thawed bottlenose dolphin (Tursiops truncatus) spermatozoa after sex-sorting and recryopreservation," Society for Reproduction and Fertility, Mar. 27, 2012, pp. 1-50.
Seidel, George E., "Sexing Mammalian Sperm—Where Do We Go From Here?" Journal of Reproduction and Development, vol. 58, No. 5, 2012, pp. 505-509.
Seidel et al., "Current status of sexing mammalian spermatozoa" Reproduction, 2002, 124, pp. 733-743.
International Search Report dated May 21, 2013 in corresponding International Application No. PCT/US13/28931.
Burroughs, C.A., "Sex-Sorting of Bovine Sperm"Colorado State University, 2011.
de Graaf, S.P., et al., "Application of seminal plasma in sex-sorting and sperm cryopreservation", Theriogenology, 70 2008, 1360-1363.
de Graaf, S.P., et al., "Birth of offspring of pre-determined sex after artificial insemination of frozen-thawed, sex-sorted and re-frozen-thawed ram spermatozoa", Theriogenology 67 2007, 391-398.
Garcia, E.M., et al. "Improving the fertilizing ability of sex sorted boar spermatozoa" Theriogenology, 68 2007, 771-778.
Presicce, G.A., et al., "First established pregnancies in Mediterranean Italian buffaloes (Bubalus bubalis) following deposition of sexed spermatozoa near the utero tubal junction", Reproduction in domestic animals 40.1 (2005): 73-75.
Strober, Warren. "Trypan blue exclusion test of cell viability", Current protocols in immunology (2001): A-3B. (2 pp).
"Characteristics of Deionised Water", 2004 (6 pp).
US FDA Brochure, "Food Color Facts", 1993 (5 pp).
Australian Patent Examination Report Issued on Jun. 26, 2015 in related AU Appl. No. 2013325222.
Office Action issued on Jul. 31, 2015 in related U.S. Appl. No. 13/784,597.
Office Action issued on May 6, 2015 in related U.S. Appl. No. 14/045,617.
Underwood et al. "In vitro characteristics of frozen-thawed, sex-sorted bull sperm after refreezing or incubation at 15 or 37°C" Theriogenology (2009) 72: 1001-1008).
Hllinshead et al. "Birth of lambs of a pre-determined sex after in vitro production of embryos using frozen—thawed sex-sorted and re-frozen—thawed ram spermatozoa" Reproduction (2004) 127: 557-568.
Johnson et al., "Improved Flow Sorting Resolution of X- & Y-Chromosome Bearing Viable Sperm Separation Using Dual Staining and Dead Cell Gating." Cytometry, vol. 17, Supplement 7, Abstract, p. 83 (1994).
Office action issued on Jan. 14, 2015 for U.S. Appl. No. 13/784,597.
International Search Report Issued on Apr. 22, 2013 in related PCT Appl. No. PCT/US13/63286.
International Search Report Issued on May 21, 2013 in related PCT Appl. No. PCT/US13/28934.
Australian Patent Examination Report Issued on Sep. 22, 2015 in related AU Appl. No. 2013325223.
New Zealand Patent Examination Report Issued on Sep. 17, 2015 in related NZ Appl. No. 630380.
New Zealand Patent Examination Report Issued on Sep. 17, 2015 in related NZ Appl. No. 630388.
New Zealand Patent Examination Report Issued on Sep. 17, 2015 in related NZ Appl. No. 630394.
Office Action issued on Sep. 28, 2015 in related U.S. Appl. No. 14/045,617.
Schenk et al. "Pregnancy Rates in Heifers and Cows with Cryopreserved Sexed Sperm: Effects of Sperm Numbers Per Inseminate, Sorting Pressure and Sperm Storage before Sorting." Theriogenology, 71, 2009, p. 717-728.
DeJarnette et al. "Evaluating the Success of Sex-Sorted Semen in US Dairy Herds From on Farm Records." Theriogenology, 71, 2009, p. 49-58.
DeJarnette et al. "Effects of 2.1 and 3.5 × 106 Sex-Sorted Sperm Dosages on Conception Rates of Holstein Cows and Heifers" J. Dairy Sci. 93, p. 4079-4085. 2010.
DeJarnette et al. "Effects of Sex-Sorting and Sperm Dosage on Conception Rates of Holstein Heifers: Is Comparable Fertility of Sex-Sorted and Conventional Semen Plausible?" J. Dairy Sci. 94, p. 3477-3483. 2011.
Frijters et al. "What Affects Fertility of Sexed Bull Semen More, Low Sperm Dosage or the Sorting Process." Theriogenology, 71, 2009, p. 64-67.
Featured Charter Sponsor—Dairy Cattle Reproduction Council. 2014. http://www.dcrcouncil.org/newsletters/2014-march/featured-charter-sponsor.aspx.
Extended European Search Report dated Feb. 5, 2016 issued in related EP 13844253.8.
Henkel, Rolf, "Sperm Preparation: State-Of-The-Art-Physiological Aspects and Application of Advanced Sperm Preparation Methods." Asian Journal of Andrology, vol. 14, No. 2, Mar. 1, 2012.
New Zealand Notice of Acceptance issued on Apr. 20, 2016 in related NZ Appl. No. 630380.
Notice of Acceptance dated Jun. 10, 2016 issued in related AU 2013325222.
Canadian Examination Report dated Jan. 18, 2016 issued in related CA 2,886,903.
European Search Report dated May 17, 2016 issued in related EP Appl. No. 13844269.4.
Canadian Office Action dated Jan. 18, 2016 issued in related CA Appl. No. 2,886,796.
New Zealand Examination Report dated Jan. 21, 2016 issued in related NZ Appl. No. 630394.
Office Action dated Jun. 16, 2016 issued in related U.S. Appl. No. 14/045,617.
New Zealand Examination Report dated Jan. 20, 2016 issued in related NZ Appl. No. 630388.
Canadian Office Action dated Jan. 18, 2016 issued in related CA Appl. No. 2,886,782.
European Search Report dated Feb. 22, 2016 issued in related EP Appl. No. 13843780.1.
Johnson, L., et al. "Preselection of Sex of Offspring in Swine for Production: Current Status of the Process and its Application." Theriogenology 63 (2005) 615-624.
Rens, Wim, et al. "Improved Flow Cytometric Sorting of X-and Y-Chromosome Bearing Sperm: Substantial Increase in Yield of Sexed Semen." Molecular Reproduction and Development 52:50-56 (1999).
European Search Report dated Jan. 29, 2016 issued in related EP Appl. No. 15186997.1.
Filho, M. et al. "Sex-Sorted Sperm for Artificial Insemination and Embryo Transfer Programs in Cattle." Anim. Reprod., /v.11, n.3, p. 217-224, Jul./Sep. 2014.
Gaviraghi, A. et al. "Minimum Number of Spermatozoa Per Dose in Mediterranean Italian Buffalo (Bubalus Bubalis) Using Sexed Frozen Semen and Conventional Artificial Insemination." Theriogenology 79 (2013) 1171-1176.
Klinc, P. et al. "Insemination with Sex Sorted Fresh Bovine Spermatozoa Processed in the Presence of Antioxidative Substances." Reprod Dom Anim 42, 58-62 (2007).
Vishwanath, R. "Sexed Sperm Vs Conventional Sperm—a Comparative Discussion." Proceedings, Applied Reproductive Strategies in Beef Cattle • Aug. 17 &18, 2015. http://appliedreprostrategies.com/2015/documents/proceedings/16bVishwanath-pg250-256.pdf.
Office Action dated Jan. 8, 2016 issued in related U.S. Appl. No. 13/784,578.

(56) References Cited

OTHER PUBLICATIONS

Australian Examination Report dated Aug. 30, 2016 issued in related NZ Appl. No. 2013327057.
Canadian Office Action dated Sep. 26, 2016 issued in related CA Appl. No. 2,886,796.
BD Influx Cell Sorter User's Guide; Becton, Dickinson and Company. 2011.
Australian Examination Report dated Apr. 18, 2016 issued in related NZ Appl. No. 2013325223.
Australian Examination Report dated Sep. 13, 2016 issued in related NZ Appl. No. 2013325223.
Canadian Office Action dated Sep. 26, 2016 issued in related CA Appl. No. 2,886,782.
Office Action dated Oct. 20, 2016 issued in related U.S. Appl. No. 14/045,617.
Canadian Office Action dated Sep. 26, 2016 issued in related CA Appl. No. 2,886,903.
New Zealand Notice of Acceptance issued on Nov. 7, 2016 in related NZ Appl. No. 630388.
Office Action dated Nov. 21, 2016 issued in related U.S. Appl. No. 13/784,578.
New Zealand Notice of Acceptance issued on Nov. 16, 2016 in related NZ Appl. No. 630394.
Australian Examination Report dated Nov. 24, 2016 issued in related AU Appl. No. 2016231560.
Australian Examination Report dated Dec. 15, 2016 issued in related AU Appl. No. 2013327057.
EP Examination Report dated Jan. 17, 2017 issued in related EP Appl. No. 13844253.8.
EP Examination Report issued on Mar. 20, 2017 in related EP Appl. No. 13843780.1.
Office Action issued on Feb. 17, 2017 in related U.S. Appl. No. 14/045,617.
Office Action issued on Mar. 29, 2017 in related U.S. Appl. No. 14/861,572.
Amirat et al. "Modifications of Bull Spermatozoa Induced By Three Extenders: Biociphos, Low Density Lipoprotein and Triladyl, Before, During and After Freezing And Thawing." Reproduction (2005), v129, p. 535-543.
Kornhauser et al. "Applications of Hydroxy Acids: Classification, Mechanisms, and Photoactivity. Clinical.", Cosmetic and Investigational Dermatology (2010), v3, p. 135-142.
EP Examination Report issued on May 8, 2017 issued in related EP Appl. No. 15186997.1.
AU Examination Report issued on May 31, 2017 issued in related AU Appl. No. 2016231560.
Office Action dated Aug. 18, 2017 issued in U.S. Appl. No. 14/045,617.
Office Action dated Sep. 25, 2017 issued in U.S. Appl. No. 14/861,572.
Office Action dated Aug. 22, 2017 issued in U.S. Appl. No. 13/784,597.
Fouz et al. Factors associated with 56-day non-return rate in dairy cattle. Pesq. agropec. bras., Brasilia (2011), v46(6), Year: 2011).
De Graaf et al. Reproduction in Domestic Ruminants VIII (Aug. 2014), p. 507-522 (Year: 2014).
Juengel et al. Reproduction in Domestic Ruminants VIII (Aug. 2014), i-vi (Year: 2014).
Canadian office Action dated Sep. 18, 2017 issued in CA Appl. No. 2,886,782.
AU Notice of Acceptance issued Apr. 18, 2018 in related AU Appl. No. 2017201275.
Office Action issued Jun. 1, 2018 in related U.S. Appl. No. 13/784,597.
EP Examination Report issued Jun. 19, 2018 in related EP Appl. No. 15186997.1.
European examination report issued on Feb. 2, 2018 in related EP application No. 13844253.8.
Office Action issued on Mar. 13, 2018 in related U.S. Appl. No. 14/861,572.
Australian Notice of Acceptance issued on Mar. 14, 2018 in related AU application No. 2015230805.
Canadian Requisition by the Examiner dated Aug. 27, 2018 issued in related CA Appl. No. 2,886,782.
Office Action dated Aug. 10, 2018 issued in related U.S. Appl. No. 14/045,617.
Canadian Requisition by the Examiner dated Aug. 10, 2018 issued in related CA Appl. No. 2,886,903.
Indian Examination Report dated Dec. 27, 2018 issued in related IN Appl. No. 951/KOLNP/2015.
European Examination Report dated May 16, 2019 issued in related EP Appl. No. 15186997.1.
Chinese Office Action dated Feb. 19, 2019 issued in related CN Appl. No. 20150827567.0.
European Extended Search Report dated Mar. 13, 2019 issued in related EP Appl. No. 19153112.8.
Brazilian Office Action dated Apr. 22, 2019 issued in related BR Appl. No. 112015007479-0.
Brazilian Office Action dated Apr. 22, 2019 issued in related BR Appl. No. 112015007480-4.
Final Office Action dated Mar. 22, 2019 issued in related U.S. Appl. No. 14/861,572.
Brazilian Office Action dated Jun. 17, 2019 issued in related BR Application No. BR122016004716-4.
Notice of Allowance dated Jul. 19, 2019 issued in related U.S. Appl. No. 13/784,597.
Office Action dated Jun. 21, 2019 issued in related U.S. Appl. No. 14/045,617.
Brazilian Office Action dated Jul. 26, 2019 issued in related BR Application No. BR112015007481-2.
Canadian Office Action dated Jun. 28, 2019 issued in related CA Application No. 2,905,670.
Canadian Office Action dated Sep. 20, 2019 issued in related CA Application No. 2,886,903.
Brazilian Office Action dated Nov. 4, 2019 issued in related BR Application No. BR122016004716-4.
Vishwanath et al. "Storage of Bovine Semen in Liquid and Frozen State." Animal Reproduction Science 62 (2000). pp. 23-53.
Ugur et al. "Advances in Cryopreservation of Bull Sperm." Front Vet Sci. 2019; 6: 268.
Murphy et al. "Rapid Sperm Concentration is Critical to Limiting the Oxidative Stress Challenge in Liquid Bull Semen." J. Dairy Sci. 96. pp. 4447-4454.

* cited by examiner

METHODS OF PROCESSING SPERM FOR SEX SORTING

TECHNICAL FIELD

Generally, this disclosure relates to staining and sorting methods, such as those used in Fluorescence Activated Cell Sorting (FACS); and more particularly, this disclosure relates to staining methods that improve the viability of sorted sperm.

BACKGROUND

Sperm sorting methods often rely on FACS for the detection of quantifiable differences in the DNA content of X-chromosome bearing sperm and Y-chromosome bearing sperm. In order to measure DNA content, a typical step in sperm sorting includes staining a sperm population with a DNA selective fluorescent dye that stoichiometrically binds to nuclear DNA. Hoechst 33342, sometimes referred to as Hoechst bisbenzimide 33342, is the most widely utilized stain because it can be used in a sufficient quantity to differentiate small variations in nuclear DNA without exhibiting the toxicity of other dyes.

Ultimately, a small variation in DNA content is quantified differentiating X-chromosome bearing sperm from Y-chromosome bearing sperm. In bovine, for example, Holstein bulls have about a 3.8% difference in DNA content, while Jersey bulls have about a 4.1% difference. Due to the inexact nature of stoichiometric DNA staining, these small differences can be difficult to ascertain. Sperm samples, even samples within a single breed, may vary a great deal in concentration, pH, motilities and morphologies. For this reason, the staining conditions which work well in one circumstance may understain or overstain other sperm samples, even sperm samples collected from the same breed, or even from the same animal. Several staining conditions may be tested before the entire sample is stained for this reason.

Unfortunately, the sperm sorting process is damaging to non-regenerative, time critical sperm cells and the staining step may be especially harmful. While Hoechst 33342 can be used in non-toxic concentrations, sperm must be incubated at elevated temperatures and elevated pHs for sufficient Hoechst 33342 penetration with sufficient uniformity for analysis or sorting. Each of elevating sperm temperature and elevating sperm pH may contribute to sperm damage. Therefore, a certain trade-off may exist between the conditions for establishing a more uniform staining and reducing the percentage of sperm damaged and killed in the sorting process.

DISCLOSURE OF INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a method of processing sperm that begins with obtaining a sperm sample. The concentration of the sperm sample may be adjusted to a predetermined concentration and the pH of the sperm sample can be adjusted towards a predetermined value before staining the sperm sample.

Another embodiment relates to a method of sorting sperm that begins by obtaining a sperm sample. The extended sperm may then be stained with a single staining buffer having a DNA selective dye and a quenching dye and the sorted.

Still another embodiment relates to a method of sorting sperm which begins by obtaining a sperm sample. The sperm sample may then be stained with a staining buffer having a DNA selective dye at an elevated pH. The sperm sample may also be stained with a quenching dye and sorted such that the elevated pH introduced with the DNA selective dye is maintained until the time of sorting.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

In certain aspects the present invention provides improved sperm treatment procedures with particular benefits to sex sorting sperm. For example, certain aspects relate to establishing a standardized sperm pH and concentration prior to additional sorting steps, such as staining. In previous methods, sperm samples having various neat pHs and concentrations may require different handling processes, which may be determined on a case-by-case basis. The standardization of ejaculates may result in more consistent staining between different samples.

Another aspect relates to maintaining a more constant pH throughout the course of staining, and even through the steps of sorting and freezing sperm. Previous sperm processing methods may have introduced sperm damage in carrying out steps which were intended to reduce sperm damage. The benefit to sperm health may be directly reflected by a reduction in the percentage of sperm which absorb dead quenching dye and are removed from the live sperm population during sorting.

Yet another aspect relates to a one step staining process which provides improved sperm viability over previous two step processes. In addition to the improved motility, a greater percentage of live sperm resulted in increased sorting rates.

Previous staining methods included two steps, typically the first step included incubation with a first buffer, and a DNA selective dye, such as Hoechst 33342, at an elevated pH and temperature. For sorting bovine, the first buffer may have an elevated pH of about 7.4. The value 7.4 may be slightly outside the range in which sperm are comfortable, but necessary to allow the DNA selective dye to permeate the sperm membrane.

After the incubation period a second staining step included the stained sperm was extended in an equal volume of a second buffer which included a dead quenching dye, such as a food dye. The second buffer may be the same buffer as the first buffer, but adjusted down to a pH of about 5.5. In this way, the 7.4 is brought back to a more physiologically acceptable value for the sperm. It was previously believed that it was more beneficial to the health of sperm to return the pH to a value near 6.8.

However, it was appreciated by applicants that the process by which the second buffer is introduced may be causing more damage than it is preventing. Specifically, as the second buffer is introduced into the sperm sample extended with the first buffer, pockets of fluid having the 5.5 pH may contact sperm cells before the mixture is evenly dispersed and the entire volume is at a single pH. The high level of acidity in the second buffer may be harmful as the second buffer is dispensed into the extended sperm sample before reaching equilibrium.

In one aspect the invention provides a method of processing sperm including the steps of: (1) obtaining a population of sperm; (2) adjusting the concentration of the sperm sample to a predetermined concentration (3) adjusting the pH of the sample to a predetermined value and (4) staining the population of sperm.

Various embodiments described herein may further include the step of sorting the stained sperm population, such as sex sorting the stained sperm population based on DNA content. In such an embodiment, the sperm sample may be maintained at, or near, the predetermined pH through the steps of staining and sorting.

Various further embodiments may include the steps of sorting sperm and freezing the sorted sperm. In such embodiments, the sperm sample may be maintained at, or near, the predetermined pH through the steps of staining, sorting, and freezing.

In another aspect the invention provides a method of selecting gender enriched populations of sperm including the steps of: (1) obtaining a population of sperm; (2) staining the sperm sample with a single staining buffer having a DNA selective dye and a quenching dye and; (3) sorting the stained sperm sample.

Various embodiments may include adjusting the sperm sample to a predetermined concentration and/or at a predetermined pH value prior to staining. The sperm may be sorted and frozen while being maintained at, or near, the predetermined pH value.

In still another aspect, the invention provides a method of processing sperm including the steps of: (1) obtaining a population of sperm; (2) adjusting the concentration of the sperm sample to a predetermined concentration (3) adjusting the pH of the sample toward a predetermined value and (4) staining the sperm sample with a single staining buffer having a DNA selective dye and a quenching dye and (5) sorting the stained sperm.

Obtaining Sperm

The population of sperm can be obtained in the form of neat semen, extended sperm, frozen-thawed sperm or in combinations thereof. The population of sperm can be obtained at the same location the remaining steps are performed, or can be extended in an appropriate sperm buffer for transport to a sorting facility. The sperm can be maintained at room temperature, chilled, or even frozen in an appropriate buffer for later use. The step of obtaining sperm can considered acquiring the sperm from a mammal, but may also include acquiring sperm from storage, such as obtaining a frozen or chilled straw from storage, or even pooling frozen or extended sperm.

The population of sperm can originate from mammals, such as a non-human mammals listed by Wilson, D. E. and Reeder, D. M., *Mammal Species of the World*, Smithsonian Institution Press, (1993), the entire contents of which are incorporated herein by reference.

At the time of collection, or thawing, or even pooling, sperm may be checked for concentration, pH, motility and/or morphology. Additionally, antibiotics may be added prior to any further processing steps.

Adjusting Sperm to a Predetermined Concentration and Towards o a Predetermined pH Once obtained, sperm may be standardized to a predetermined concentration and/or towards a predetermined pH. Each of the predetermined concentration and pH, may be specific to different species, or even to different breeds of animals within a species. In one embodiment, the sperm may be combined with an initial buffer in the form of a high capacity buffer. Examplary buffers may include TRIS citrate, sodium citrate, sodium bicarbonate, HEPES, TRIS, TEST, MOPS, KMT, TALP and combinations thereof. Any buffer having a high capacity for buffering pH may also be employed, and may be used in combination with additional components which promote sperm viability such as egg yolk, and sources of citrates or citric acid. Additionally, antioxidants and antibiotics may be employed in the initial buffer to promote sperm viability.

The initial buffer may be set at a predetermined pH to normalize the pH of all the obtained sperm samples. In one embodiment, the buffer is adjusted to a pH of 7.2. Additionally, semen may become increasingly acidic over time, possibly because of proteins in the seminal fluid, or possibly due to acidic byproducts of dead or dying cells. In either case, the initial buffer introduces enough free proton (e.g. $H^+$) binding sites to maintain pH near the predetermined target. Even in light of the natural tendency for sperm to become more acidic over time, the initial buffer provides a means for stabilizing pH throughout additional processing steps.

As one example, the sperm sample may be diluted in the high capacity buffer in ratios from about 1:1 to about 1:10. The resulting mixture will have a sperm concentration many times below natural sperm concentrations for a particular species. The extended sperm may be centrifuged in order to reconcentrate sperm. Centrifuging the sperm and removing supernatant allows the sperm to be reconcentrated into a predetermined concentration. The predetermined concentration may be selected based on additional sperm processing steps. For example, in the case of sex sorting bovine, sperm may be reconcentrated at between about 2400 million sperm per ml and about 900 million sperm per ml to simulate a natural range of concentrations. Other concentrations, such as between about 1400 million sperm per ml and about 2100 million sperm per ml may or between about 1700 million sperm per ml and about 2100 million sperm per ml may also be achieved for further processing.

Adjusting the sperm concentration and pH may provide a uniform starting point for further processing. For example, a relatively consistent pH and concentration may provide greater predictability in staining sperm, for example with a DNA selective dye. If each sample is adjusted to the same predetermined pH and concentration, fewer trials may be required on each new collection to ensure adequate staining for sex sorting.

Staining the Sperm

The sperm sample can include X-chromosome bearing sperm and Y-chromosome bearing sperm. Additionally, each of the X-chromosome bearing sperm and the Y-chromosome bearing sperm can include viable sperm and nonviable sperm. Viable sperm can be considered sperm with intact membranes while nonviable sperm can be considered sperm with compromised membranes. Viable sperm, in the appropriate dosage, will generally be capable of achieving fertilization in an artificial insemination, while nonviable sperm, or membrane compromised sperm, may be incapable of achieving fertilization in an artificial insemination or will have a greatly reduced ability to do so. However, some sperm capable of fertilization may have compromised membranes, and some sperm with intact membranes may be incapable of fertilization.

Whether standardized or not, sperm may be stained with a staining buffer for introducing a DNA selective dye. In the staining step, at least a portion of the population of sperm is incubated with a staining buffer and a DNA selective fluorescent dye in order to stoichiometrically stain the DNA content of each cell in the sperm population. Hoechst 33342 is most commonly used in the field of sperm sorting, as it tends to be less toxic than other DNA selective dyes. The vehicle for delivering this dye may be in the form of a modified TALP buffer adjusted to a pH of about 7.4. Hoechest 33342 is described in U.S. Pat. No. 5,135,759, and is commonly used for this purpose. However, other UV excitable dyes, as well as visible light excitable dyes, fluorescent polyamides, fluorescent nucleotide sequences, and sex specific antibodies could also be used.

Sperm in a natural state is often not readily permeable to such dyes. In order to produce a uniform staining, the first step of staining can include incubating at least a portion of the sperm population at an elevated temperature in a staining buffer at an elevated pH in addition to the dye. Examples of appropriate first staining buffers can be a TALP, TES-TRIS, TRIS citrate, sodium citrate, or a HEPES based medium, each described in WO2005/095960, incorporated herein by reference. An examplary modified TALP described in WO2001/37655, incorporated herein by reference, is illustrated in Table 1.

TABLE 1

Modified TALP buffer

| Ingredient | Concentration |
|---|---|
| NaCl | 95.0 mM |
| KCl | 3.0 mM |
| NaHPO$_4$ | 0.3 mM |
| NaHCO$_3$ | 10.0 mM |
| MgCL$_2$ 6H$_2$O | 0.4 mM |
| Na Pyruvate | 2.0 mM |
| Glucose | 5.0 mM |
| Na Lactate | 25.0 mM |
| HEPES | 40.0 mM |
| bovine serum albumin | 3.0 mg/ml |

As one example, the population of sperm, or a portion of the population of sperm, could be diluted with the first buffer to between 640×10$^6$ and 40×10$^6$ sperm/ml, to between about 320×10$^6$ and 80×10$^6$ sperm/ml, or to about 160×10$^6$ sperm/ml in the first buffer. The DNA selective fluorescent dye can be added to the sperm suspended in the first buffer in a concentration of between about 10 µM and 200 µM; between about 20 µM and 100 µM, or between about 30 µM and 70 µM. The pH of the first buffer can be between about 6.8 and 7.9; about 7.1 and 7.6; or at about 7.4 in order to help ensure a uniform staining of nuclear DNA. Those of ordinary skill in the art will appreciate the pH can be elevated with the addition of NaOH and dropped with the addition of HCl.

The population of sperm can be incubated between 30-39° C., between about 32-37° C., or at about 34° C. The period of incubation can range between about 20 minutes and about an hour and a half, between about 30 minutes and about 75 minutes, or for about 45 minutes to about 60 minutes. As one example, the population of sperm can be incubated for about 45 minutes at 34° C. Even within a single species, sperm concentration and pH and other factors affecting stainability can vary from animal to animal. Those of ordinary skill in the art can appreciate minor variations for incubating sperm between species and even between breeds or animals of the same breed to achieve uniform staining without over staining a population of sperm.

In addition to the DNA selective fluorescent dye a quenching dye may be applied for the purpose of permeating membrane compromised sperm and quenching the signals they produce. A dead quenching dye can be understood to include dyes which differentially associate with membrane compromised sperm. It may be that these dyes enter membrane compromised sperm cells more easily because the membranes are breaking down or otherwise increasingly porous, but it may also be that dead quenching dyes readily enter all sperm cells and that healthy sperm cells act to pump dead quenching dyes out faster than membrane compromised sperm. In either case, the sperm cells with which the dead quenching dyes associate includes a large portion of dead and dying sperm cells, although not necessarily all dead and dying sperm cells. The quenched signals produced from membrane compromised sperm having an association with quenching dye are distinct enough from the signals of healthy sperm that they may be removed from the analysis and sorting of viable sperm.

In one embodiment, the quenching dye and the DNA selective dye are applied together in a single treatment. In this embodiment, the quenching dye is incubated along with the DNA selective dye at an elevated temperature in the modified TALP which may be at a pH of 7.4. In this embodiment is believed a synergy exists when the sperm standardized at an elevated pH of about 7.2 before staining at 7.4. In this way, the pH to which the sperm is exposed remains in a constant range with minimal variations. Because both the staining buffer and the initial extender have high buffering capacities, it is believed the natural tendency of sperm to become more acidic over time will be avoided. Additionally, by minimizing the changes in pH seen by the sperm, it is believed the sperm are in a healthier condition to face the various pressures and stresses endured in the sex sorting process.

Sorting Stained Sperm

Figure 1:
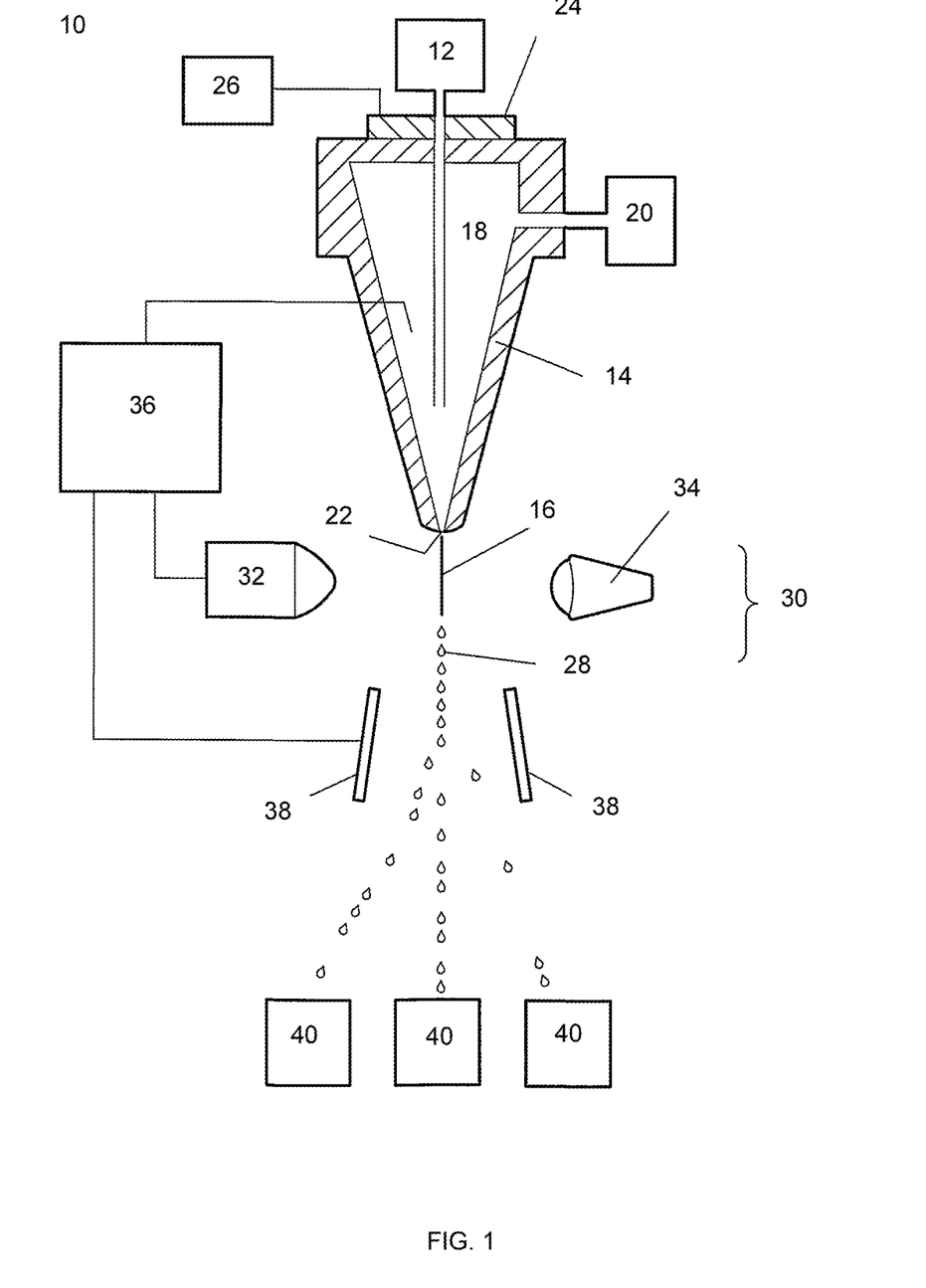
FIG. 1 illustrates a schematic of a flow cytometer for sorting sperm in accordance with certain embodiments of the invention.
Figure 2:
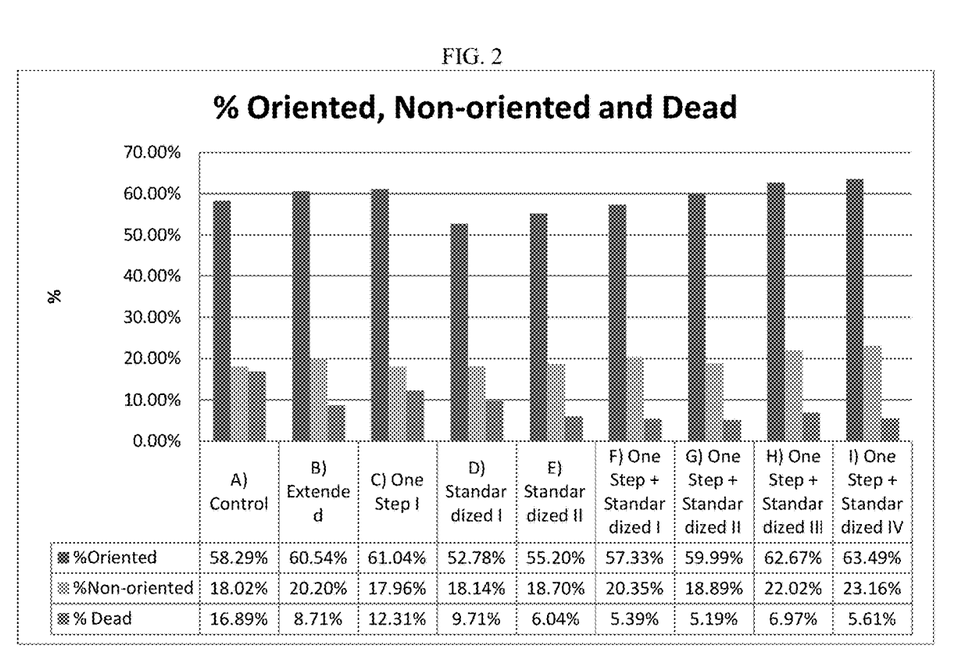
FIG. 2 illustrates a graphical representation of various sort parameters acquired in a flow cytometer while sorting sperm prepared and stained according to various embodiments of the present invention.

The stained sperm population can be sorted by flow cytometry. Referring now to FIG. 1, a jet-in-air flow cytometer (10) is illustrated, although sorting may be performed with microfluidic chips or other types of flow cytometers. The flow cytometer (10) includes a cell source (12) supplying the stained sperm sample for sorting. The stained sperm are deposited within a nozzle (14) and introduced into a fluid stream (16) of sheath fluid (18). The sheath fluid (18) can be supplied by a sheath fluid source (20) so that as the cell source (12) supplies the sperm into the sheath fluid (18) they are concurrently fed through the nozzle (14). In this manner the sheath fluid (18) forms a fluid stream coaxial to the sample having stained sperm. Since the various fluids are provided to the flow cytometer (10) at some pressure, they flow out of nozzle (14) and exit at the nozzle orifice (22). By providing an oscillator (24) which may be precisely controlled with an oscillator control (26), pressure waves may be established within the nozzle (14) and transmitted to the fluids exiting the nozzle (14) at nozzle orifice (22). In response to the pressure waves, the fluid stream (16) exiting the nozzle orifice (22) eventually forms regular drops (28) at precise intervals. Because the stained sperm are surrounded by the fluid stream (16) or sheath fluid environment, the drops (28) may contain individually isolated sperm.

The flow cytometer (10) acts to sort drops based on the characteristics of sperm predicted to be contained within the drops. This is accomplished through a cell sensing system (30). The cell sensing system (30) includes at least a sensor (32) responsive to the cells contained within fluid stream (16). The cell sensing system (30) may cause an action depending upon the relative presence or relative absence of a characteristic. Certain characteristics, such as the relative DNA content of sperm cells, can be detected through excitation with an electromagnetic radiation source (34), such as a laser generating an irradiation beam to which the stained sperm are responsive. The electromagnetic radiation source (34) can be a laser operated at UV wavelength, such as at about 355 nm. An example of such a laser can be a Vanguard 350 (available from Spectra-Physics), which operates at 350 mW. Various optics may be employed to shape the beam profile of the laser, split the beam to more than one stream, or reduce the beam power at a stream. Non-limiting examples of such optics can be found in WO/2004/104178 and WO/2001/85913, each being incorporated herein by reference.

The characteristics of individual sperm, particularly the presence of an X-chromosome or a Y-chromosome can be determined from the detected fluorescence produced in response to the electromagnetic radiation source (34). The DNA selective fluorescent dye binds stoichiometrically to sperm DNA. Because X-chromosome bearing sperm contain more DNA than Y-chromosome bearing sperm, the X-chromosome bearing sperm can bind a greater amount of DNA selective fluorescent dye than Y-chromosome bearing sperm. Thus, by measuring the fluorescence emitted by the bound dye upon excitation, it is possible to differentiate between X-bearing spermatozoa and Y-bearing spermatozoa.

In order to achieve separation and isolation based upon stained sperm characteristics, emitted light can be detected by the sensor (32) and the information fed to an analyzer (36) coupled to a droplet charger which differentially charges each drop (28) based upon the characteristics of the stained sperm contained within that drop (28). In this manner the analyzer (36) acts to permit the electrostatic deflection plates (38) to deflect drops (28) based on whether or not they contain the appropriate particle or cell.

As a result, the flow cytometer (10) acts to separate stained sperm by causing the drops (28) containing sperm to be directed to one or more collection containers (40). For example, when the analyzer differentiates sperm cells based upon a sperm cell characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus be collected in an undeflected stream into a suction tube or the like as discussed in U.S. patent application Ser. No. 09/001,394, hereby incorporated by reference herein. Naturally, numerous deflection trajectories can be established and collected simultaneously.

Example 1

Standardizing Sperm Samples and One Step Staining

Collection—Sperm was collected from five different bulls on a routine collection schedule using an artificial vagina. Each bull was collected 2 or three times in one day. Of the five bulls, two were Jersey bulls and three were Holstein bulls. All ejaculates contained greater than 60% progressive motility and sperm concentration varied from 857 million sperm per mL to 2480 million sperm per mL. Ejaculates collected from the same bull were pooled then divided into nine sperm samples for collection and staining treatments.

Staining—Portions of each bull ejaculate were stained with nine different methods.

(A) Control (no standardization, two step staining)—A control was established which did not include the step of standardizing collected ejaculates and in which the sperm was stained in two steps. Prior to staining, the sperm samples were concentrated to between 1700 million sperm per mL and 1800 million sperm per mL by centrifugation or by the addition of a tris-egg yolk buffer having a pH of 6.8, depending on the samples starting concentration.

Sperm in the control group was diluted to $160 \times 10^6$ sperm per ml in a modified TALP buffer, as described in Table 1, at a pH of 7.4. Each sperm sample in the control group was then incubated with 16-17 µL of Hoechst 33342 per ml (64-68 µM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 µM yellow food dye No. 6 (20 g/L) and the pH was dropped to 5.5 with the addition of HCl.

(B) Extended (no standardization, two step staining)—In the second group, sperm was not standardized, but was extended with a buffer and 20% egg yolk. The sperm was then concentrated to between 1700 million sperm per mL and 1800 million sperm per mL in the same manner described with respect to group (A). The sperm was then diluted to $160 \times 10^6$ sperm per ml in a modified TALP buffer, and stained in the same two step manner described in group (A).

(C) One Step I (no standardization, one step staining with 1% egg yolk)—In a third group sperm was collected and the concentration was adjusted in the same manner as the control group (A). Each sperm sample was then diluted to $160 \times 10^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 µM. Each sperm sample in this group was then incubated with 14-15 µL of Hoechst 33342 per ml (46-60 µM) for 45 minutes at 34° C. After incubation, sperm remained at a concentration of $160 \times 10^6$ sperm per ml.

(D) Standardized I (standardized with 3% egg yolk buffer, two step staining)—In this group sperm was standardized by adjusting both the pH and sperm concentration prior to staining and sorting. After collection sperm was diluted 1:3 in an initial buffer having a pH of 7.2 as well as a high capacity for buffering pH. The high capacity buffer was supplemented with 3% egg yolk. All samples were then centrifuged to bring the sperm concentration down to between 1700 million sperm and 1800 million sperm per mL. The standardized sperm was then stained according to the two step method described in (A).

(E) Standardized II (standardized with 10% egg yolk buffer, two step staining)—In this group sperm was standardized by adjusting both the pH and sperm concentration prior to sorting in the same manner described in group (D), except that the initial buffer was 10% egg yolk.

(F) One Step and Standardized I (standardized with 3% egg yolk buffer, one step staining with 1% egg yolk)—In this group sperm was standardized by adjusting both the pH and sperm concentration prior to sorting in the same manner described in group (D). The standardized sample was then stained with a one step staining process as described in group (C).

(G) One Step and Standardized II (standardized with 10% egg yolk buffer, one step staining with 1% egg yolk)—In this group sperm was standardized by adjusting both the pH and sperm concentration prior to staining in the same manner described in group (E). The standardized sample was then stained with a one step staining process as described in group (C).

(H) One Step and Standardized III (standardized with 3% egg yolk buffer, one step staining with no egg yolk)—In this group sperm was standardized by adjusting both the pH and sperm concentration prior to staining in the same manner described in group (D). The standardized sample was then stained with a one step staining process as described in group (C), except that no egg yolk was added to the one step staining TALP.

(I) One Step and Standardized IV (standardized with 10% egg yolk buffer, one step staining with no egg yolk)—In this group sperm was standardized by adjusting both the pH and sperm concentration prior to sorting in the same manner described in group (E). The standardized sample was then stained with a one step staining process as described in group (C) except that no egg yolk was added to the one step staining TALP.

Sorting and data acquisition—Each of the stained samples was sorted on a MoFlo SX (Beckman Coulter, USA). Those samples which were stained in a two step process were sorted at the concentration of $80 \times 10^6$ sperm per mL, and those samples which were stained by the one step process were sorted at the concentration of $160 \times 10^6$ sperm per mL. Data logged by the flow cytometer was recorder including information relating to the sort rates and gating of sperm subpopulations. For example, the percentage of sperm gated as dead, as well as the percentages of sperm gated as live-oriented and over ranges were recorded and averaged for the five bulls.

Results—A comparison of the percentage of sperm which was orientated, unoriented and dead as determined by the sort parameters established in the flow cytometer are summarized in Table 2 below.

TABLE 2

| | % Oriented | % Non-oriented | % Dead | Sort Rate | Over-range |
|---|---|---|---|---|---|
| A) Control | 58.29% | 18.02% | 16.89% | 3500 | 4.32% |
| B) Extended | 60.54% | 20.20% | 8.71% | 3400 | 10.36% |
| C) One Step I | 61.04% | 17.96% | 12.31% | 3500 | 5.65% |
| D) Standardized I | 52.78% | 18.14% | 9.71% | 2900 | 24.73% |
| E) Standardized II | 55.20% | 18.70% | 6.04% | 3200 | 23.44% |
| F) One Step + Standardized I | 57.33% | 20.35% | 5.39% | 3200 | 16.17% |

TABLE 2-continued

| | % Oriented | % Non-oriented | % Dead | Sort Rate | Over-range |
|---|---|---|---|---|---|
| G) One Step + Standardized II | 59.99% | 18.89% | 5.19% | 3600 | 16.83% |
| H) One Step + Standardized III | 62.67% | 22.02% | 6.97% | 3800 | 6.23% |
| I) One Step + Standardized IV | 63.49% | 23.16% | 5.61% | 4100 | 5.38% |

As compared to the control (A), the groups One Step I (C), Standardized I (D), and Standardized II (E), each exhibited significantly lower dead populations with reductions of 4.58%, 7.18% and 10.85%, respectively. Based on these improvements, the steps of standardizing sperm samples before staining and modifying the staining process to a single step independently improve the ability of sperm to survive the sorting process. Additionally, One Step and Standardized I (F), One Step and Standardized II (G), One Step and Standardized III (H), and One Step and Standardized IV (I), demonstrate a synergy whereby the combined effect of standardizing an ejaculate and staining the ejaculate in a single step is greater than either improvement individually.

Referring to Table 2, it can be seen that Standardize I (D), Standardize II (E), One Step and Standardized I (F), and One Step and Standardized II (G), each appeared to provide significant benefits in terms reducing the number of dead sperm, but the percentage of oriented sperm did not improve. This may be related to the column indicated as over rage. While more sperm were gated as live for sorting there appears to be an increase in signals scattered above the sorting gate ranges. This signal may represent sperm which is stuck together or may represent sperm which is bound to egg yolk lipids. In either event, the general pattern emerges that greater quantities of egg yolk reduce dead sperm numbers, but may introduce a new issue and a balance may therefore be required.

Example 2

Standardizing Sperm Samples and One Step Staining

Collection—Sperm was collected from six different Jersey bulls on a routine collection schedule using an artificial vagina. All ejaculates contained greater than 65% progressive motility and sperm concentration varied from 765 million sperm per mL to 1710 million sperm per mL. Each Sperm sample was divided into two parts in 15 mL tubes for two collection and staining treatments. pH measurements were taken at collection, and at each subsequent processing step.

Staining—

Control (no standardization, two step staining)—A control was established which did not include the step of standardizing collected ejaculates and in which the sperm was stained in two steps. Prior to staining, the sperm samples were concentrated to between 1700 million sperm per mL and 1800 million sperm per mL by centrifugation or by the addition of a tris-egg yolk buffer having a pH of 6.8, depending on the samples starting concentration.

Sperm in the control group was diluted to $160 \times 10^6$ sperm per ml in a modified TALP buffer, as described in Table 1, at a pH of 7.4. Each sperm sample in the control group was then incubated with 16-17 µL of Hoechst 33342 per ml (64-68 µM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 µM red food dye No. 40 (20 g/L) and the pH was dropped to 5.5 with the addition of HCl.

One Step and Standardized (standardized with 10% egg yolk, one step staining with one percent egg yolk)—Sperm was standardized by adjusting both the pH and sperm concentration prior to staining. After collection sperm was diluted 1:3 in an initial buffer having a pH of 7.2 as well as a high capacity for buffering pH. The high capacity buffer was supplemented with 3% egg yolk. All samples were then centrifuged to bring the sperm concentration down to between 1700 million sperm and 1800 million sperm per mL.

The sperm samples were then diluted to $160 \times 10^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 µM. Each sperm sample in this group was then incubated with 16-17 µL of Hoechst 33342 per ml (64-68 µM) for 45 minutes at 34° C. After incubation, sperm remained at a concentration of $160 \times 10^6$ sperm per ml.

Sorting and data acquisition—Each sample was sorted on a MoFlo SX (Beckman Coulter, USA). The control was sorted at the concentration of $80 \times 10^6$ sperm per mL, while the standardized sperm was sorted at $160 \times 10^6$ sperm per mL. Data was logged by the flow cytometer and then averaged for the 6 bulls.

Figure 3:
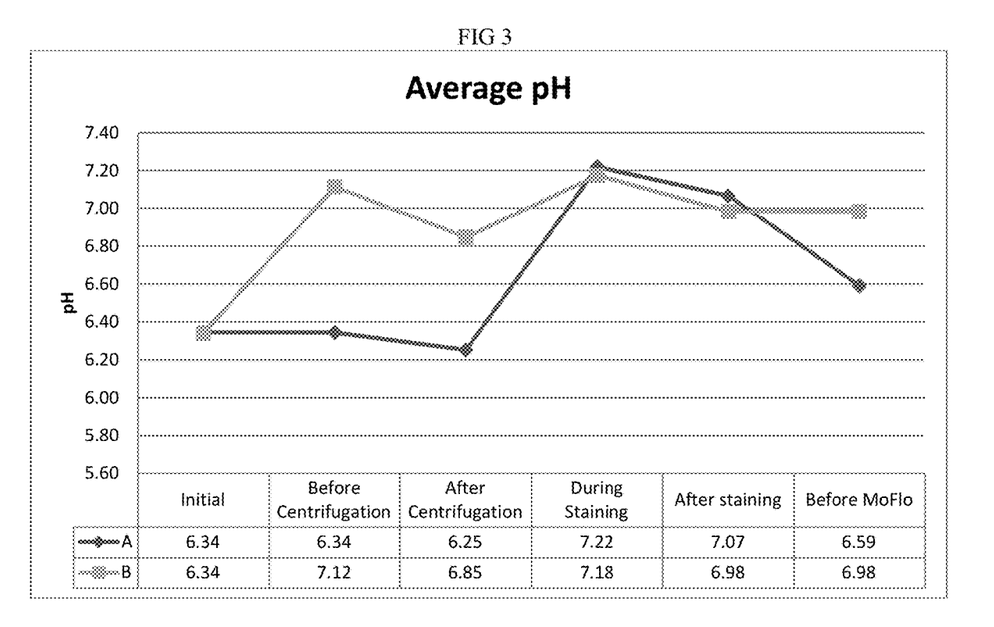
FIG. 3 illustrates a graphical representation of pH values acquired during a sperm preparation and staining.

Results—FIG. 3 illustrates the recorded pH of both the control (A) and the standardized ejaculate (B). These Values are reflected in TABLE 3 below. While the standardized ejaculate is subject to an initial increase, a subsequent increase is avoided during staining and the following drop off is also avoided. Additionally, TABLE 4 illustrates similar benefits in the reduction of dead sperm that was seen in Example 1. Specifically, the standardized sample which was stained in one step had 5.67% less dead sperm.

TABLE 3

|  | Initial | Before Centri- fugation | After Centri- fugation | During Staining | After staining | Before cytometer |
|---|---|---|---|---|---|---|
| Control (A) | 6.34 | 6.34 | 6.25 | 7.22 | 7.07 | 6.59 |
| Standardized (B) | 6.34 | 7.12 | 6.85 | 7.18 | 6.98 | 6.98 |

TABLE 4

|  | PV | % Oriented | % Dead | Sort Rate | Duplets/ Triplets |
|---|---|---|---|---|---|
| Control | 1.86 | 52.99 | 14.63 | 35.83 | 21.73 |
| Standardized – One Step | 1.97 | 57.22 | 8.96 | 37.00 | 24.59 |
| Difference | 0.11 | 4.23 | −5.67 | 1.17 | 2.86 |

As can be easily understood from the foregoing, the basic concepts of the present invention may be embodied in a variety of ways. The invention involves numerous and varied embodiments of staining sperm for sex sorting including, but not limited to, the best mode of the invention.

As such, the particular embodiments or elements of the invention disclosed by the description or shown in the figures or tables accompanying this application are not intended to be limiting, but rather examplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. A method comprising:
   extending a bovine sperm sample in an initial extender at a sperm sample to initial extender ratio between about 1:1 and 1:10;
   reconcentrating the extended bovine sperm sample to a concentration between 900 million sperm per ml and 2400 million sperm per ml, wherein the reconcentrated bovine sperm sample concentration is higher than the concentration of the extended bovine sperm sample following extension in the initial extender;
   diluting the reconcentrated bovine sperm sample with a volume of staining buffer to a concentration between about 80 million sperm per ml and 320 million sperm per ml and adding a DNA selective dye;
   staining the diluted bovine sperm sample;
   determining the presence of an X or Y chromosome in the stained bovine sperm sample; and
   collecting a population of viable X-chromosome bearing sperm and/or viable Y-chromosome bearing sperm.

2. The method of claim 1, wherein the volume of staining buffer comprises modified TALP with a pH of 7.4.

3. The method of claim 1, wherein the DNA selective dye comprises Hoechst 33342.

4. The method of claim 1, further comprising adding a quenching dye comprising yellow food dye No. 6.

5. The method of claim 1, further comprising the step of sorting the stained sperm with a flow cytometer.

6. The method of claim 1, wherein the pH of the bovine sperm sample is maintained at a target pH from the dilution step through the determination step.

7. The method of claim 6, wherein the pH of the bovine sperm sample is maintained within 0.5 of the target pH from the dilution step through the determination step.

8. The method of claim 5, wherein the pH of the bovine sperm sample is maintained between 6.75 and 7.3 from the step of diluting through the step of sorting.

9. The method of claim 5, further comprising the step of freezing sorted sperm.

10. The method of claim 9, wherein the pH of the sperm sample is maintained at the same target pH through each of the steps of staining, sorting, and freezing.

11. The method of claim 1, wherein the initial extender comprises a pH buffering extender.

12. The method of claim 1, wherein the initial extender comprises one or more selected from the group of: sodium bicarbonate, TRIS citrate, sodium citrate, HEPES, TRIS, TEST, MOPS, KMT, and combinations thereof.

13. The method of claim 12, wherein the initial extender further comprises egg yolk.

14. The method of claim 13, wherein the initial extender further comprises between about 1 percent and 10 percent egg yolk.

15. The method of claim 12, wherein the initial extender further comprises citric acid or citrates.

16. The method of claim 12, wherein the initial extender further comprises one or more antioxidants.

17. The method of claim 12, wherein the initial extender has a pH of 7.2.

18. The method of claim 1, wherein the step of reconcentrating the bovine sperm sample further comprises:
   centrifuging the extended sperm sample; and
   removing supernatant.

19. The method of claim 1, wherein the DNA selective dye is contained in the staining buffer.

20. The method of claim 5, further comprising reconcentrating the sorted sperm to a concentration suitable for freezing.

21. The method of claim 1, wherein the sperm are reconcentrated to between 900 million sperm per ml and 2400 million sperm per ml in the same extender as the initial extender.

22. A method comprising:
   extending a bovine sperm sample in an initial extender to an extended concentration;
   reconcentrating the extended bovine sperm sample to a concentration higher than the extended concentration;
   diluting the reconcentrated bovine sperm sample with a volume of staining buffer to a concentration between about 80 million sperm per ml and 320 million sperm per ml;
   staining the diluted bovine sperm sample with a DNA selective dye;
   determining the presence of an X or Y chromosome in the stained bovine sperm sample; and
   collecting a population of viable X-chromosome bearing sperm and/or viable Y-chromosome bearing sperm.

* * * * *